United States Patent [19]
Woosley et al.

[11] Patent Number: 5,711,966
[45] Date of Patent: Jan. 27, 1998

[54] METHOD OF TREATING MALARIA WITH DESBUTYLHALOFANTRINE

[76] Inventors: Raymond Woosley, 2720 Chain Bridge Rd., NW., Washington, D.C. 20016; David L. Wesche, 1618 Tilton Dr., Silver Spring, Md. 20902; Brian G. Schuster, 1620 Crowell Rd., Vienna, Va. 22182

[21] Appl. No.: 703,595

[22] Filed: Aug. 23, 1996

[51] Int. Cl.⁶ ..................................... A61K 9/48
[52] U.S. Cl. ........................... 424/451; 514/895
[58] Field of Search ........................ 424/451, 464, 424/422; 514/895, 649; 564/355

[56] References Cited

U.S. PATENT DOCUMENTS 5,250,234  10/1993  Rossignol et al. ............... 564/355

OTHER PUBLICATIONS

Colwell, et al., *Journal of Medicinal Chemistry*, 1972, vol. 15, No. 7.

*Primary Examiner*—Edward J. Webman
*Attorney, Agent, or Firm*—Glenna Hendricks; Carol Carr

[57] ABSTRACT

This invention provides a method of treating patients suffering from malaria whilst avoiding cardioarrhythmias, the improvement thereof comprising the administration of desbutylhalofantrine in place of halofantrine. Dosage of 500 mg every six hours for three doses on day one with repeat of that dosage on day 7 for a total dosage of 3000 mg is appropriate for most treatment purposes in adults. Desbutylhalofantrine may also be given at dosage of 50 to 1000 mg as a prophylactic measure. Dosage may be given daily or one day per week.

7 Claims, No Drawings

METHOD OF TREATING MALARIA WITH DESBUTYLHALOFANTRINE

This application takes priority for the Provisional Application accorded the identifying number 60/002,819 which was filed on Aug. 25, 1995.

FIELD OF THE INVENTION

This invention is related to improved compositions for treatment of malaria.

BACKGROUND OF THE INVENTION

Halofantrine has been used for treatment of malaria caused by *Plasmodium falciparum*. The most commonly administered active agent is halofantrine HCl usually given in a dosage of 500 mg every 6 hours for three doses on day 1 followed by repeat dosing seven days later. U.S. Pat. No. 5,250,734 to Rossignol, et al discloses analogues of halofantrine, including desbutylhalofantrine. However, he teaches that the desbutylhalofantrine is less effective than halofantrine for treatment of malaria. No reason is suggested for giving desbutylhalofantrine in place of halofantrine.

Halofantrine, while useful for treatment of malaria, has been shown to cause cardiotoxicity. A common problem associated with drugs used to treat malaria are their effects on cardiac repolarization as reflected by prolongation of the QT interval. The arrhythmias caused thereby are often life-threatening. The arrhythmia known as torsades de pointes has been seen in patients receiving quinine, quinidine, chloroquine and halofantrine. The arrhythmias can result in sudden death of the patients.

The discovery that halofantrine can induce potentially fatal arrhythmias has lead authorities to urge caution in administration of halofantrine.

DESCRIPTION OF THE INVENTION

This invention provides a method of treating patients suffering from malaria whilst avoiding cardioarrhythmias, the improvement thereof comprising the administration of desbutylhalofantrine in place of halofantrine. The patent cited previously discloses desbutylhalofantrine, but does not claim its use. Furthermore, the patent to Rossignol suggests that desbutylhalofantrine is less useful than halofantrine. Hence, one would not be encouraged thereby to replace use of halofantrine with desbutylhalofantrine on the basis of the teachings found in that patent disclosure. It has now been found that desbutylhalofantrine of the structure:

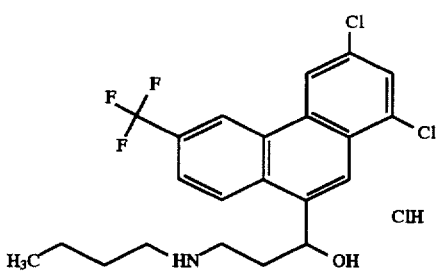

possesses many of the desirable qualities of halofantrine, whilst avoiding the cardiotoxicity that so frequently accompanies treatment with halofantrine when given in antimalarial-effective amounts.

Comparative studies evaluating prolongation of the QT interval using quinidine, halofantrine, and desbutylhalofantrine were performed on isolated perfused animal hearts. It was found, surprisingly, that the major metabolite of halofantrine, desbutylhalofantrine, did not prolong the QT interval even when concentrations were increased to twenty fold the concentration at which halofantrine resulted in prolongation of the QT interval. The ability to treat malaria with this metabolite without causing cardiotoxicity greatly improves the safety of antimalarial treatment.

MATERIALS AND METHODS

A comparison of the parent drug, halofantrine with the metabolite desbutylhalofantrine was conducted to determine which agent was primarily responsible for QT interval prolongation. The effects of halofantrine and its active metabolite (N-desbutylhalofantrine) on repolarization were examined in an isolated perfused heart model. In the isolated perfused heart, halofantrine was able to prolong the QT interval, whereas desbutylhalofantrine had minimal effect on the QT interval relative to the baseline. In an attempt to further elucidate the mechanism for QT interval prolongation, the effects of racemic halofantrine, its stereoisomers and N-desbutylhalofantrine on repolarizing currents in isolated ventricular myocytes were studied using patch-clamp techniques.

Isolated perfused heart model:

The effects of halofantrine and its metabolite on repolarization were examined in the isolated perfused cat heart by the method of Woosley, et al. (*JAMA* 269:1532–1536 (1993)). Briefly, hearts were obtained from healthy, mature anesthetized cats and perfused in a Lagendorff apparatus maintained at 37° C. A pacing electrode was placed in the right ventricular apex and stimulated at 40 msec cycle lengths using a cardiac stimulator. The AV node was destroyed by cautery to produce complete heart block and allow observations at slow cycle lengths. Electrodes were placed in the bath and positioned for recording of an orthogonal electrocardiogram (ECG) that allowed accurate measurement of the QT interval. All data were stored on a personal computer for later final analysis.

After a 20-minute period for stabilization, the QT intervals were observed until three separate recordings (2–3 minutes apart) indicated the presence of stable measurements (<5% change). Recordings of QT intervals were obtained after 30 seconds of pacing at a cycle length of 400 msec. When the recordings had returned to stable baseline, the perfusion solution was changed to include halofantrine HCl or N-desbutylhalofantrine HCl at concentrations of from 1 to 20 µM. QT interval recordings were obtained continuously for 30 seconds every 5 minutes for forty minutes. The concentration was then increased to the next highest level for the next forty minutes. Recordings were again made the same cycle length. Cardiac conduction and rhythm were observed and changes, if they occurred, were noted. Concentrations were selected that could best delineate the concentration/response curve for each drug.

Individual Cardiac Myocytes:

The cardiac electro-pharmacologic effects of halofantrine, its stereoisomers and N-desbutylhalofantrine on repolarizing currents such as the delayed rectifier potassium channel were studied in feline ventricular myocytes in vitro by the method described by Woosley, et al. (*JAMA* 269:1532–1536 (1993)). Briefly, rod-shaped and quiescent ventricular cells were obtained and used for electrophysiological recordings using the whole cell, single-suction pipette, voltage-clamp ("patch-clamp") technique. Computer-controlled voltage clamp pulses (duration 750 ms) were used to elicit currents. Current signals were directed to a computer for storage and data analysis. Calculation of the percentage block of peak $I_k$ currents was made comparing baseline to the peak heights after drug administration for each cell.

Results:

Halofantrine produced a stereo-selective block of the delayed rectifier potassium channel in isolated feline myocytes, indicating that this drug is similar to Class III antiarrhythmics in its ability to prolong repolarization.

N-desbutylhalofantrine was made in accord with the following procedure:

2-nitro-4-trifluoromethylphenyl acetic acid (1)

To a cooled (0°) solution of 4-trifluoromethylphenylacetic acid (550 g; 1.45 mol) in sulfuric acid (2.0 L) was added, over 1.5 hours, nitric acid (90%; 300 mL) at such a rate as to maintain the temperature between 0° and 5° C. The solution was stirred for 15 minutes, then poured into ice water (17 L). The solid that separated was collected on a filter, washed with water (2 times with 2.5 L, by resuspension), then dissolved in ether (3.0 L). The ethereal solution was washed with water (2 times with 1.0 L), dried, then concentrated in vacuo. The last traces of water were removed by co-distillation with ethanol (500 mL). Yield: 588.2 g (96.4%). The material was suitable for further transformation. Additional product (116.6 g) was obtained from a scouting run.

2,4 dichloro-2'-nitro-4'-trifluoromethylphenylcinnamic acid (2)

A mixture of 2-nitro-4-trifluoromethylphenylacetic acid (588.2 g; 2.36 mol), 2,4-dichlorobenzaldehyd (413 g; 2.36 mol), acetic anhydride (597 mL), and potassium carbonate (182.4 g; 1.32 mol) was heated to 65° C. An exotherm occurred and the temperature rose to 80° C. The reaction mixture was stirred at 65° C. for 2 hours, cooled, diluted with water (3.0 L), followed by addition of 1% hydrochloric acid (1.5 L) and stirred for 1 hour. The solid that precipitated was collected, dried in vacuo at 100° C., then recrystallized from toluene (15.0 L). Yield: 682.9 g (71.2%). This material was suitable for further transformation. Additional product (124.2 g) was obtained from a scouting run.

2,4 dichloro-2'-amino-4'-trifluoromethylphenycinnamic acid. sodium salt (3)

To a hot (80° C.) solution of ferrous sulfate, heptahydrate (1676 g; 6.03 mol) and sodium hydroxide (725 g; 18.13 mol) in water (7 L) was added a warm suspension of 2,4-dichloro-2'- nitro-4'-trifluoromethylphenylcinnamic acid (245.1 g, 0.603 mol) in water (1 L). The mixture was heated at 100° C. for 0.5 hour, then filtered hot through a pad of Celite. The filtrate was cooled, and the solid that separated was collected, washed with water (2 times with 300 mL), then dried by co-distillation with toluene. Yield: 217.3 g (90.5%). The material was suitable for further transformation. Additional product (467 g) was obtained from two similar runs and a scouting run.

1,3-dichloro-6-trifluoromethyl-9-phenanthroic acid (4)

To a cooled (−5° C.) suspension of 2,3-dichloro-2'-amino-4'- trifluoromethylphenylcinnamic acid, sodium salt (211 g; 0.530 mol) and isoamylnitrite (210.0 g; 244.8 mL; 180 mol) in ethanol (1.8 L) was added, over a period of 1 hour, 17% solution of hydrochloric acid in ethanol (1477 mL). The suspension was stirred for 2 hours −5° C. to 0° C., then added to a warm (40° C.) mixture of sodium dihydrogen phosphate (544 g; 6.3 mol), copper bronze (24.5 g) and sulfuric acid (34 drops) in water (844 mL), and the resulting suspension was stirred for one hour. The solid was collected on a filter, then washed with ethanol (400 mL). The filter cake was suspended in $H_2O$ (1 L), and the insolubles were filtered off. The insolubles were suspended in EtOH (500 mL), then concentrated in vacuo to a solid. The solid was suspended in THF (350 mL, and the insoluble material was filtered off, then discarded. The filtrate was concentrated in vacuo to a solid. Yield: 84.5 g (44.4%). The material was suitable for further transformation. Additional product (177.2 g) was obtained from two similar runs and a scouting run.

1.3-dichloro-6-trifluoromethvl-9-hydorxymethyphenanthrene(5)

To a cold (0° C. to 5° C.) 1 molar solution of borane in tetrahydrofuran (800 mL; 0.8 mol) was added, dropwise, under an argon atmosphere, a solution of 1,3-dichloro-6-trifluoromethyl- 9-phenanthroic acid (240 g; 0.668 mol) in tetrahydrofuran (2400 mL). The resulting mixture was stirred at room temperature for one hour, refluxed for 2 hours, then cooled. Excess borane was decomposed by the addition of water (210 mL). The solvent was removed in vacuo and the residue was washed with boiling water (4 L), then dried. Yield: 207.0 g (90.8%). Additional product (18.8 g) was obtained from a scouting run. The two lots were combined, then recrystallized from EtOH (6 L). Yield: 191.3 g. (84.4% recovery). The product was suitable for further transformation.

1.3-dichloro-6-trifluoromethvl-9-phenanthrenebarboxaldehyde (6)

To a cold (0° C. to 5° C.) solution of 1,3-dichloro-6-trifluoromethyl-9-heydroxymethylphenanthrene (184.7 g; 0.535 mol) in pyridine (4.8 L, saturated with argon prior to the addition of the phenanthrene) was added lead tetraacetate (487.7 g; 1.10 mol). The mixture was stirred at room temperature for 5 hours, then diluted with water (5.6 L). The solid was collected on a filter, dried, then extracted with THF (4 times with 2 L). The extracts were combined, then concentrated in vacuo to a solid (172.5 g). The solid was purified on a column of silica gel (2.5 kg) using EtOAc as the eluent. Fractions containing the product were combined, concentrated in vacuo, and the residue was triturated with EtOH (2.0 L). The solid was collected, then dried. Yield: 144.3 g (78.6%). The material was suitable for further transformation. Additional product (15.2 g) was obtained from a scouting run.

N-butylacetamide (7)

Butylamine (75.g; 1.025 mol) was cooled to −30° C. in a dry ice/acetone bath, and glacial acetic acid (902.4 g, 1.54 mol) was added dropwise over a 1.5 hour period. The mixture was removed from the cooling bath and acetic anhydride (104.6 g; 1.1025 mol) was added dropwise over a 2 hour period. A slight exotherm was observed. The acetic acid was distilled off, and the product collected. Yield: 110.3 g (93.5%); bp 112°/3.51 mm; (literature bp 125°/13 mm).

3-3(1,3-dichloro-6-trifluoromethyl-9-phenanthryl)-3-hydroxy-N- (n-butyl)propionamide (8)

To a cold, stirred (−5° C.) solution of N-butylacetamide (75.9 g; 0.668 mol) in tetrahydrofuran (2.0 L) was added, dropwise, a solution of 2.5M n-butyllithiumin hexane (534 mL; 1.336 mol). The mixture was stirred at −5° C. for one hour. To the resulting suspension was added, dropwise, a solution of 1,3-dichloro-6-trifluoromethyl-9-phenantrenecarboxaldehyde (144.3 g; 0.420 mol) in tetrahydrofuran (2.2 L). The mixture was stirred at −5° C. for one hour, then at room temperature for 16 hours followed by heating at 50° C. for one hour. The resulting dark brown solution was cooled in ice and diluted with aqueous ammonium acetate (5.0 L, 15%). The organic layer was separated from the aqueous layer. The aqueous solution was then extracted with ethyl acetate (3 times with 1 L). The combined organic solutions were evaporated to dryness, and the resulting yellow solid was triturated with methanol (1200 mL) to give 188 g of crude product. This product was then combined with 10.7 g of similar material obtained from a scouting run. The combined material was dissolved in THF (500 mL) and the solution was mixed with silica gel (500 g) and concentrated in vacuo to a powder. The powder was divided into 2 equal portions. Each portion was applied onto a 2.0 kg silica gel column (hexane-EtOAc 1:1) and eluted with hexane EtOAc 1:1, 35.0 L). Fractions containing product and slight impurities were combined, then concentrated in vacuo to a solid. Yield: 140.9 g (66.3%). This material was suitable for further transformation.

1.3-dichloro-6-trifluoromethyl-9-[1-hydroxy-3-(N-n-butylamino)- propyl]phenanthrene hydrochloride(9) (desbutylhalofantrine HCl)

To a cold (−5° C.) solution of 1M borane (1060 mL; 1.06 mol) in tetrahydrofuran, under an argon atmosphere was added a solution of 3-(1,3)dichloro-6-trifluoromethyl-9-phenathryl-3- hydroxy-N-(n-butyl)propionamide (120.6 g; 0.263 mol) in tetrahydrofuran (4.0 L) at such a rate that the temperature did not exceed 0° C. After the addition, the reaction mixture was allowed to warm to room temperature for one hour, and was then refluxed for 22.5 hours. Excess borane was decomposed by adding 240 mL of 50% aqueous tetrahydrofuran dropwise followed by 1420 mL of water containing 382 mL of concentrated hydrochloric acid. The tetrahydrofuran was distilled off at atmospheric pressure. The precipitated solid was collected and recrystallized from ethanol (2.5 L) to give 96.4 g (76.7%) of product. A second crop (6.8 g) increased yield to 82.1%. Additional material (13.5 g) was obtained from a scouting run. Analytically pure material (104.2 g; 89.3% recovery) was obtained by recrystallizing 116.7 g of the solid ethanol (4.0 L). The mp (observed) was 281°–281° C. (Literature mp is 275°–279° C.).

|  | Analysis of product: | | | | |
|---|---|---|---|---|---|
|  | C | H | N | Cl | F |
| Calculated | 55.25 | 4.83 | 2.93 | 21.72 | 11..92 |
| Found | 55.23 | 4.86 | 2.80 | 21.52 | 11.68 |

Spectral Data:
Infrared (Noujol)
Major bands at: 3300, 2900, 2800, 1625, 1585, 1450, 1370, 1345, 1310, 1280, 1165, 1135, 1115, 1070, 885, 835 cm$^1$.

EXAMPLES

Capsules of a formulation of desbutylhalofantrine for oral administration is prepared by mixing 250 mg desbutylhalofantrine, 245 mg starch and 5 mg. magnesium stearate. Two capsules are administered six hours apart three times on day one. The regimen is repeated on day six.

To provide a liquid emulsion, the following are mixed:

| N-desbutylhalofantrine free base | 10 g. |
|---|---|
| Ethyl alcohol | 15 ml |
| Glycerol | 5 ml |
| Sorbitol | 2 ml |
| Water | to 100 ml. |

Five ml of the emulsion is administered six hours apart three times on day one. The same dosage is administered on day six.

The desbutylhalofantrine may be administered in protected forms such as in microdroplets, microcrystals or in liposomes using protective materials such as lipids or lecithin. Compositions may also be prepared using cyclodextrin inclusion complexes of the desbutylhalofantrine. Such compositions containing the active agent in protected form may be prepared from the free base and may be administered parenterally. The ability to administer compositions intravenously to patients unable to accept medicaments by oral route provides new possibilities for treatment.

The desbutylhalofantrine is approximately equipotent with the parent compound against various clones of *Plasmodium falciparum* in in vitro studies and may be administered in accord with the methods used to administer halofantrine. Dosage of 500 mg every six hours for three doses on day one with repeat of that dosage on day 7 for a total dosage of 3000 mg is appropriate for most treatment purposes in adults. However, total dosage range of 50 to 5000 mg can be given depending on the condition, age and size of the patient. Desbutylhalofantrine may also be given at dosage of 50 to 1000 mg as a prophylactic measure. Dosage may be given daily or one day per week. Again, dosage will be determined by the clinician in accord with the needs of the particular patient. When given as a prophylactic agent, the administration may be continued for several months.

Desbutylhalofantrine may be given as the free base or the salt of any acid. It may be administered orally as a capsule, tablet, elixir, suspension or emulsion. Alternatively, desbutylhalofantrine may be mixed with lipid for oral administration in elixirs, emulsions, suspensions or in capsules. For intravenous administration a salt of desbutylhalofantrine may be administered in solution. The free base would be administered as a solution in lipid or, alternatively, in alphatocopherol. The lipid vehicle may contain mono-, di- or tri-glycerides with fatty acids of varying lengths.

We claim:

1. A method of preventing malaria or treating patients suffering from malaria whilst avoiding cardiac arrhythmias, the improvement thereof comprising the administration of desbutylhalofantrine in an anti-malarial effective amount in place of halofantrine.

2. A method of claim 1 wherein the desbutylhalofantrine is administered to patients suffering from malaria.

3. A method of claim 1 wherein the 50 to 5000 mg total dosage is administered with ½ of the dosage given on day 1 and ½ of the dosage is given on day 7 of the treatment.

4. A method of claim 1 wherein the desbutylhalofantrine is given to prevent malaria and dosage is 50 to 1000 mg. daily or weekly.

5. A method of claim 4 wherein the desbutylhalofantrine is given daily.

6. A method of claim 4 wherein the desbutylhalofantrine is given weekly.

7. A method of claim 3 wherein the total dosage is about 3000 mg.

* * * * *